United States Patent [19]

Bear et al.

[11] Patent Number: 5,756,989
[45] Date of Patent: May 26, 1998

[54] COLOR NIGHT VISION GOGGLES CAPABLE OF PROVIDING ANTI-JAMMING PROTECTION AGAINST PULSED AND CONTINUOUS WAVE JAMMING LASERS

[75] Inventors: Philip D. Bear, Godfrey, Ill.; Larry C. Walrath, Kirkwood, Mo.

[73] Assignee: McDonnell Douglas Corporation, St. Louis, Mo.

[21] Appl. No.: 755,213

[22] Filed: Nov. 22, 1996

[51] Int. Cl.$^6$ ........................................... H01J 40/14
[52] U.S. Cl. .............................. 250/214 VT; 313/526; 348/217; 250/226
[58] Field of Search ........................ 250/207, 214 VT, 250/216, 226; 313/525–528; 348/216, 217

[56] References Cited

U.S. PATENT DOCUMENTS

| | | | |
|---|---|---|---|
| 5,001,558 | 3/1991 | Burley et al. | 348/164 |
| 5,162,647 | 11/1992 | Field, Jr. | 250/214 VT |
| 5,214,503 | 5/1993 | Chiu et al. | 348/217 |
| 5,233,183 | 8/1993 | Field | 250/214 VT |
| 5,262,880 | 11/1993 | Abileah | 349/64 |

*Primary Examiner*—Stephone B. Allen
*Attorney, Agent, or Firm*—Robert Westerlund

[57] ABSTRACT

Color night vision goggles (NVG), e.g., binocular-style or monocular-style NVG, which include at least one channel. Each channel includes an objective lens for receiving input radiant energy from a low-luminance scene within the field-of-view of the NVG, an input tunable electro-optical filter positioned in front of the objective lens, an image intensifier device for amplifying input radiant energy transmitted by the input electro-optical filter and the objective lens, and for generating output radiant energy which constitutes an amplified image of the low-luminance scene, an eyepiece lens, an output tunable electro-optical filter disposed between the image intensifier device and the eyepiece lens, and a control circuit for generating a control signal having a prescribed frequency. The input and output electro-optical filters sequentially and synchronously transmit successive ones of a plurality of different spectral bands (e.g., the blue, green, and red color bands) of the input and output radiant energy, respectively, in response to the control signal, during each successive cycle of the control signal, whereby a viewer can perceive a full-color image of the low-luminance scene when looking through the eyepiece lens. The prescribed frequency of the control signal is preferably sufficiently high to ensure that the full-color image is flicker-free. The color NVG are preferably further provided with a gated power supply for supplying current to the image intensifier device, a detector for detecting laser light that may enter the field-of-view of the NVG and for producing a train of electrical output pulses in response to detection of laser light, even when the detected laser light is generated by a continuous wave laser, and a pulse-following circuit responsive to the train of electrical output pulses produced by the detector for producing a corresponding train of gating pulses. The gated power supply is responsive to the gating pulses for selectively interrupting the current supplied by the gated power supply in synchronism with the detected laser pulses, to thereby protect the color NVG from all possible jamming laser threats.

20 Claims, 2 Drawing Sheets

COLOR NIGHT VISION GOGGLES CAPABLE OF PROVIDING ANTI-JAMMING PROTECTION AGAINST PULSED AND CONTINUOUS WAVE JAMMING LASERS

BACKGROUND OF THE INVENTION

The present invention relates generally to the field of night vision goggles, and more particularly, to color night vision goggles which provide a viewable color display of a low-luminance, night scene being viewed by the wearer and which provide anti-jamming protection against all possible laser threats.

Night vision goggles (NVG) have gained notoriety since their deployment in the Persian Gulf war. The most prevalent type (Type 1) of NVG are binocular-style NVG, which have a pair of parallel optical channels, one for each eye. In overview, for each optical channel, the radiant energy from the low-luminance scene being viewed is focused by an objective lens onto an image intensifier tube of an image intensifier device, e.g., an image intensifier device of the type manufactured by Litton and ITT. The image intensifier tube includes a photocathode which is composed of a photosensitive material. The photosensitive material of the photocathode releases electrons in an amount proportional to the intensity of the incident radiant energy.

The image intensifier device also includes a microchannel plate provided with a multiplicity of microchannels through which pass the electrons released by the photosensitive material of the photocathode of the image intensifier tube. The microchannels of the microchannel plate act as an electron gain medium, so that the electrons which pass therethrough stimulate the release of a cascade of additional electrons. The amplified streams of electrons which are produced by the microchannels of the microchannel plate of the image intensifier device form an intensified/amplified electron image of the low-luminance scene being viewed by the wearer of the NVG.

The NVG further include a phosphor-coated display screen which is excited by the electrons produced by the image intensifier device. The excited phosphor emits visible light having an intensity proportional to the number of electrons per unit time which are incident thereupon. Thus, the phosphor-coated display screen produces an intensified/amplified visible image of the low-luminance scene which may contain as much as six orders of magnitude more radiant energy than the input radiant energy from the scene.

The wearer of the NVG views this intensified/amplified visible image of the low-luminance scene produced by the phosphor-coated display screen through an eyepiece, which in the case of the binocular-style (Type 1) NVG, includes a pair of lenses, one for each eye. Thus, it can be appreciated that the image intensifier device greatly amplifies visible and infrared radiation from the scene being viewed to thereby dramatically increase the brightness of the scene as viewed by the wearer of the NVG, thus making possible activities under low-luminance, night time conditions which were impossible or impractical prior to the advent of NVG.

Some of the most prevalent applications of NVG include, without limitation, military aircrew performing night-time bombing missions, police helicopter pilots performing night-time manhunt operations, and Coast Guard crew performing night-time anti-drug trafficking operations. In addition to these non-civilian applications, NVG have several civilian applications, e.g., various activities which take place outdoors under low-luminance, night-time conditions, such as hiking, fishing, hunting, flying, boating, sailing, camping, etc.

Although the presently available NVG of the type described above have proven quite useful, they suffer from at least two significant shortcomings. The first shortcoming of the presently available NVG is that the intensified/amplified visible image of the low-luminance scene produced by the phosphor-coated display screen thereof is monochromatic, and thus appears to the viewer as varying intensity of a single color, typically green. Obviously, color NVG which provide a viewable color display of a low-luminance, night scene would constitute a major improvement over the presently available monochromatic NVG. The second shortcoming of the presently available NVG, especially those used for military and law enforcement applications, is that they are susceptible to being interfered with or "jammed" by non-cooperative (hostile) laser sources, which can produce very bright spots in the viewed image of the scene which can effectively obscure the scene being viewed by the wearer of the NVG and cause severe damage to the image intensifier tube and other components of the NVG. In this connection, it is now possible to jam current night vision goggles with relatively inexpensive jamming laser sources.

The first shortcoming has not been addressed prior to the advent of the present invention. With respect to the second shortcoming, an invention entitled "Circuit and Method for Preventing Laser Jamming of Night Vision Goggles" which addresses this shortcoming has been disclosed in co-pending U.S. patent application Ser. No. 08/697,875, to Kintz et al., which is assigned to the present assignee, and which is herein incorporated by reference. According to this invention, laser pulses from a jamming laser source are detected by a photodetector device which produces a train of electrical pulses in response to the detected laser pulses. The train of electrical pulses are synchronized with the incoming laser pulses by means of a phase-locked loop (PLL), the output of which is used to gate off the image intensifier tube in synchronism with the laser pulses. Thus, the laser pulses are not amplified by the image intensifier device, and the laser pulses are effectively prevented from adversely affecting the intensified image of the scene viewed by the wearer of the NVG, thus defeating the laser jamming countermeasure. Further, since the image intensifier tube of the NVG is only gated off for 1–2 ms, at a repitition frequency of 4–40 Hz, the gating off of the image intensifier tube is completely transparent to the wearer of the NVG, i.e., the display is flicker-free. In this connection, the gating off of the image intensifier tube can be effected by interrupting the current which is supplied to the image intensifier tube by the power supply for the tube.

Although the above-described Kintz et al. circuit provides effective protection against pulsed laser threats, it makes no provision for protection against continuous wave laser threats. Obviously, NVG which are capable of blocking both pulsed and continuous wave lasers, and thus providing anti-jamming protection against all possible laser threats, would constitute a major improvement over the presently available NVG.

Based on the above and foregoing, it can be appreciated that there presently exists a need in the art for night vision goggles which overcome the above-described shortcomings of the presently available night vision goggles. More particularly, there presently exists a need in the art for color night vision goggles which provide a viewable color display of a low-luminance, night scene being viewed by the wearer and which provide anti-jamming protection against all possible laser threats. The present invention fulfills this need in the art.

SUMMARY OF THE INVENTION

The present invention encompasses, in one of its aspects, color night vision goggles (NVG), e.g., binocular-style or monocular-style NVG, which include a pair of parallel optical channels, each of which includes an objective lens for receiving input radiant energy from a low-luminance scene within the field-of-view of the NVG, an input tunable electro-optical filter positioned in front of the objective lens, an image intensifier device for amplifying input radiant energy transmitted by the input electro-optical filter and the objective lens, and for generating output radiant energy which constitutes an amplified visible image of the low-luminance scene, an eyepiece lens, an output tunable electro-optical filter disposed between the image intensifier device and the eyepiece lens, and a control circuit for generating a control signal having a prescribed frequency. The input and output electro-optical filters sequentially and synchronously transmit successive ones of a plurality of different spectral bands (e.g., the blue, green, and red color bands) of the input and output radiant energy, respectively, in response to the control signal, during each successive cycle of the control signal, whereby a viewer can perceive a full-color image of the low-luminance scene when looking through thec eyepiece lens. The prescribed frequency of the control signal is preferably sufficiently high to ensure that the full-color image is flicker-free.

In accordance with another aspect of the present invention, the color NVG are preferably further provided with a gated power supply for supplying current to the image intensifier device, a detector for detecting laser light within a field encompassing the field-of-view of the NVG and for producing a train of electrical output pulses in response to detection of laser light (or an image tube current detector indicating the presence of the laser light), even when the detected laser light is generated by a continuous wave laser, and a pulse-following circuit responsive to the train of electrical output pulses produced by the detector for producing a corresponding train of gating pulses. The gated power supply is responsive to the gating pulses for selectively interrupting the current supplied by the gated power supply in synchronism with the detected laser pulses, to thereby protect the color NVG from all possible jamming laser threats.

BRIEF DESCRIPTION OF THE DRAWINGS

These and various other features and aspects of the present invention will be readily understood with reference to the following detailed description read in conjunction with the accompanying drawings, in which.

DETAILED DESCRIPTION OF THE INVENTION

Figure 1:
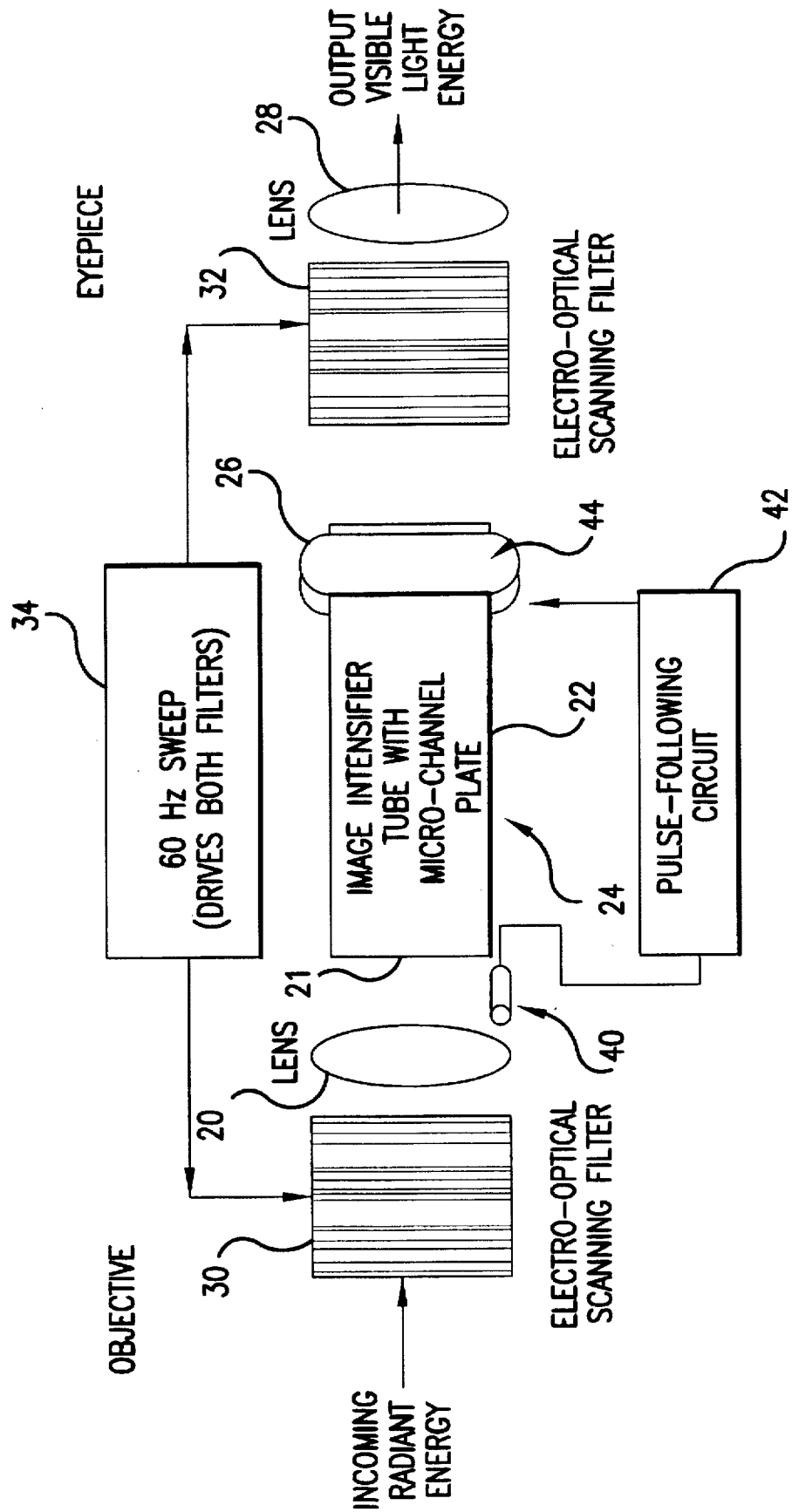
FIG. 1 is a block diagram of one of the two identical optical channels of binocular-type (Type 1) night vision goggles constructed in accordance with a presently preferred embodiment of the instant invention; and, FIG. 2 is a combined graph which includes middle and lower graphs which depict the spectral transmission characteristics of the input and output tunable electro-optical input filters of the optical channel of the night vision goggles depicted in FIG. 1, as a function of time, and an upper graph which depicts the relationship between the voltage level of the sweep signal and the spectral transmission characteristics of the input and output tunable electro-optical filters as a function of time.

With reference now to FIG. 1, the color night vision goggles (NVG) of the present invention will now be described. In a presently preferred embodiment, the color NVG of the present invention are binocular-type (Type 1) NVG, although this is not limiting to the present invention, e.g., the present invention is equally applicable to monocular-style NVG. As was described hereinabove, binocular-type NVG have two parallel optical channels, one for each eye. Although FIG. 1 depicts only one of the two optical channels of the color NVG of the present invention, since both of the optical channels are identical, the description of the one optical channel is equally applicable to the other optical channel.

In overview, for each optical channel, the radiant energy from a low-luminance scene being viewed by the wearer of the NVG is focused by an objective lens 20 onto a front face 21 of an image intensifier tube 22 of an image intensifier device 24 of a conventional type, e.g., an image intensifier device of the type manufactured by Litton and ITT. The operation of the image intensifier device 24 is the same as previously described in connection with the discussion of the presently available technology. To summarize, the photosensitive material of the photocathode of the image intensifier tube 22 releases electrons in response to the radiant energy incident on the front face 21 of the image intensifier tube 22. The image intensifier device 24 further includes a microchannel plate (not separately shown) provided with a multiplicity of microchannels through which pass the electrons released by the photosensitive material of the photocathode of the image intensifier tube. The microchannels of the microchannel plate act as an electron gain medium, so that the electrons which pass therethrough stimulate the release of a cascade of additional electrons. The amplified streams of electrons which are produced by the microchannels of the microchannel plate of the image intensifier device 24 form an intensified/amplified electron image of the low-luminance scene being viewed by the wearer of the NVG.

The NVG further include a phosphor-coated display screen 26 which is excited by the electrons produced by the image intensifier device 24. The excited broadband phosphor of the display screen 26 emits visible light having an intensity proportional to the number of electrons per unit time which are incident thereupon. Thus, the phosphor-coated display screen 26 produces an intensified/amplified visible image of the low-luminance scene which may contain as much as six orders of magnitude more output radiant energy than the input radiant energy from the scene.

The wearer of the NVG views this intensified/amplified visible image of the low-luminance scene produced by the phosphor-coated display screen 26 through an eyepiece, which in the case of the binocular-style (Type 1) NVG, includes a pair of lenses, one for each eye. The eyepiece lens 28 for one of the optical channels is shown in FIG. 1. Thus, it can be appreciated that the image intensifier device 24 greatly amplifies visible and infrared radiation from the scene being viewed to thereby dramatically increase the brightness of the scene as viewed by the wearer of the NVG, thus making possible activities under low-luminance, night time conditions which were impossible or impractical prior to the advent of NVG.

With continuing reference to FIG. 1, in accordance with a first aspect of the present invention, additional electro-optical elements are provided in order to provide full-color vision enhancement of the conventional NVG. More particularly, in accordance with this first aspect of the present invention, each optical channel of the color NVG further includes an input wavelength-tunable electro-optical filter 30 positioned in front of the objective lens 20, an output wavelength-tunable electro-optical filter 32 positioned between the phosphor-coated display screen 26 and the eyepiece lens 28 (i.e., positioned behind the eyepiece lens 28), and a control circuit 34 which sequentially and synchronously steps the input and output electro-optical (E-O) filters 30 and 32 through different spectral regions or bands of the input and output radiant energy at a sufficiently high rate (e.g., 20–180 Hz) to ensure that the actual image viewed by the wearer of the color NVG is a flicker-free, full-color image of the low-luminance scene within the field-of-view of the color NVG.

In the presently preferred embodiment, the different spectral bands of the input radiant energy are three successive bands, I1, I2, and I3, respectively, in the visible and near-infrared region of sensitivity of the photosensitive material of the photocathode of the image intensifier tube 22, and the different spectral bands of the output radiant energy are the blue (B), green (G) and red (R) wavelength/color bands. The process of sequentially stepping the input and output E-O filters 30 and 32 through the different spectral bands can be thought of as a "temporal scanning" process, and will be referred to hereinafter as such. The input and output E-O filters 30 and 32 can be thought of as "temporally scanned spectral transmission filters", in that they are driven in such a manner as to sequentially transmit different spectral (color) bands of the input and output radiant energy (within the response range of the system), respectively, in respectively sequential time intervals.

More particularly, in the presently preferred embodiment, the control circuit 34 generates a control signal (preferably a voltage signal) having a frequency within the range of 20–180 Hz, e.g., 60 Hz. This 60 Hz control signal can be thought of as a 60 Hz "sweep signal", and will hereinafter be referred to as such. The sweep signal is applied to a control input of both the input and output E-O filters 30 and 32 in order to control the spectral transmission characteristics thereof in a manner which will be more fully described hereinafter. The sweep signal may suitably be a sawtooth or stepped (staircase) voltage waveform. For purposes of the present disclosure, it is intended that the general terminology "ramp-shaped waveform" broadly encompass both sawtooth and stepped waveforms. However, it should be clearly understood that the specific type of sweep signal which is utilized is not limiting to the present invention.

Figure 2:
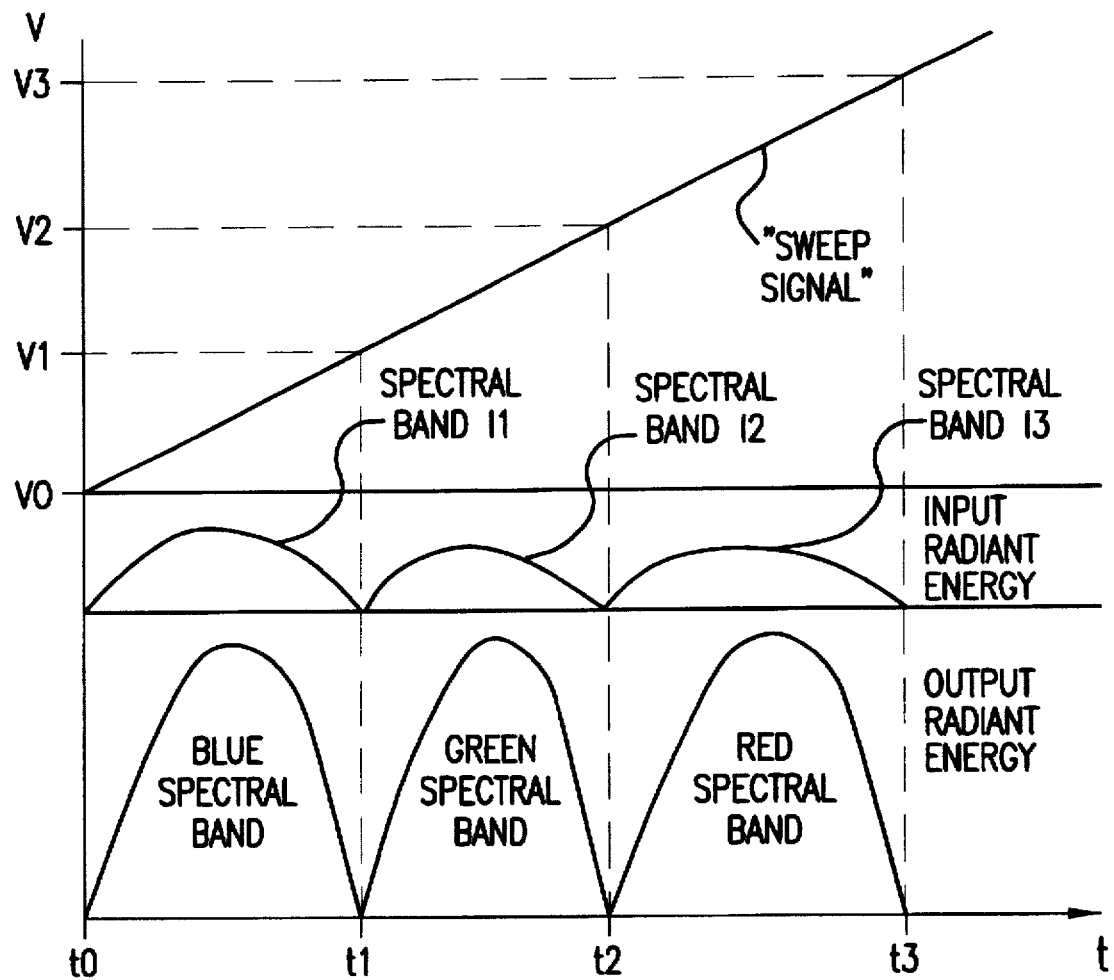

In this connection, the spectral transmission characteristics of the input and output E-O filters 30 and 32 as a function of time is depicted in the middle and lower graphs of FIG. 2, respectively. The upper graph of FIG. 2 depicts the voltage level of an exemplary sawtooth-shaped sweep signal. As can be readily ascertained from the combined graphs of FIG. 2, the voltage level of the sweep signal determines the spectral transmission characteristics of the input and output E-O filters 30 and 32. More particularly, during a first time interval t0-t1, corresponding to a voltage level of the sweep signal of between V0-V1, the input and output E-O filters 30 and 32 transmit the band I1 of the input radiant energy and the blue color band of the output radiant energy, respectively; during a second time interval t1-t2, corresponding to a voltage level of the sweep signal of between V1-V2, the input and output E-O filters 30 and 32 transmit the band I2 of the input radiant energy and the green color band of the output radiant energy, respectively; and, during a third time interval t2-t3, corresponding to a voltage level of the sweep signal of between V2-V3, the input and output E-O filters 30 and 32 transmit the band I3 of the input radiant energy and the red color band of the output radiant energy, respectively.

Thus, the three different spectral bands (I1, I2, and I3) of the input (incoming) radiant energy from the low-luminance scene being viewed are sequentially transmitted through the input E-O filter 30 during each cycle of the sweep signal, during the successive time intervals t0-t1, t1-t2, and t2-t3, respectively, and the three different color bands (blue, green, and red) of the output radiant energy (i.e., the visible monochromatic radiant energy produced by the spectrally broadband phosphor of the display screen 26) are sequentially transmitted through the output E-O filter 32 during each cycle of the sweep signal, during the successive time intervals t0-t1, t1-t2, and t2-t3, respectively. Assuming a 60 Hz sweep signal is utilized, each of the different colors of the visible radiant energy produced by the phosphor-coated display screen 26 reach the viewer's eyes in rapid succession, 60 times per second, and accordingly, the viewer's eyes fuse the successive single-color images together so that they appear to the viewer as a single, flicker-free, full-color image, in much the same way as sequentially excited blue, green, and red phosphors on the face of the CRT of a television set or RGB monitor are perceived by the viewer as a single, flicker-free, full color image. This feature of the present invention constitutes a significant advancement in the art of NVG.

Although the specific type of wavelength-tunable E-O filters which are employed is not limiting to the present invention, suitable wavelength-tunable E-O filters which may be employed include those manufactured by Displaytech and Reliant Technologies. The E-O filters manufactured by these two companies consist of stacked polarizers (both colored and neutral), ferroelectric liquid crystal half-wave plates, and supporting glass plate structure. The polarization of the incoming radiant energy received by the E-O filter of this type is dependent upon the voltage applied to the ferroelectric liquid crystal half-wave plates, and thus, the spectral transmission characteristics of the E-O filter of this type is a function of the voltage applied to the ferroelectric liquid crystal half-wave plates, i.e., the E-O filter of this type is wavelength-tunable. Accordingly, by applying a sweep signal such as a sawtooth voltage waveform to the ferroelectric liquid crystal half-wave plates, the E-O filter of this type can be temporally scanned in the manner described hereinabove.

With continuing reference to FIG. 1, in accordance with a second aspect of the present invention, the color NVG are provided with an anti-laser jamming subsystem. The anti-laser jamming subsystem is suitably of the type disclosed in the previously referenced U.S. patent application Ser. No. 08/697,875, to Kintz et al., which was filed on Aug. 30, 1996. More particularly, each channel of the color NVG is provided with an optical bright source (laser) detector 40 which is positioned between the objective lens 20 and the image intensifier device 24 to detect a portion of the incoming radiant energy that passes through the input E-O filter 30 and the objective lens 20. Alternatively, each channel of the color NVG can be provided with a high current pulse detector which is integral to the power supply 44 for detecting the presence of a bright source (e.g., a laser).

A pulse-following circuit 42 is coupled to the output of the bright source detector 40. Due to the temporal scanning of the input E-O filter 30, the incoming radiant energy which is incident upon the bright source detector 40 during each incremental scanning time interval (e.g., t0-t1, t1-t2, or t2-t3) lies within a single spectral (color) band. As such, even bright light issued by a continuous wave laser (which lies within only one of the three spectral bands transmitted by the input E-O filter 30) reaches the bright source detector 40 in the form of discrete pulses. When the bright source detector 40 receives such a train of laser pulses, it produces a corresponding train of electrical output pulses which are supplied to the pulse-following circuit 42.

The pulse-following circuit 42 controls a gated power supply 44 for the image intensifier device 24 in such a manner as to gate off (shut off) the image intensifier tube and microchannel plate of the image intensifier device 24 in synchronism with the laser pulses detected by the bright source detector 40, thereby preventing the pulses from being amplified by the image intensifier tube and microchannel plate of the image intensifier device 24. Thus, the spectral or color band of the incoming radiant energy that includes the wavelength of the jamming laser source is effectively blocked, and the phosphor of the display screen 26 is not excited thereby, so that no visible image is produced during the time intervals when the input E-O filter 30 is tuned to that color band. In effect, a fixed portion of the spectrum of the incoming radiant energy from the low-luminance scene being viewed is eliminated.

It can thus be appreciated that the above-described anti-laser jamming subsystem which constitutes the second aspect of the present invention provides protection against both pulse and continuous wave jamming laser sources, which is not possible using the the system disclosed in the previously referenced U.S. patent application Ser. No. 08/697,875, to Kintz et al. alone. This constitutes a significant advancement in the art of NVG.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

For example, by adding neutral density filters to the objective end of the system, the present invention could be employed for daytime laser eye protection. More particularly, the neutral density filters would reduce the level of the incoming radiation from a scene being viewed to a level that could be handled by the image intensifier tubes. Further, the neutral density filters would reduce the level of any incident laser energy, thereby reducing the likelihood of any damage to the image intensifier tubes. The operation of the color daytime vision goggles (DVG) would in other respects be the same as the operation of the color NVG of the present invention, as described hereinabove.

What is claimed is:

1. Color night vision goggles, comprising:
   at least one channel, each said channel including:
   an objective lens for receiving input radiant energy from a low-luminance scene within a field-of-view of the goggles;
   an input tunable electro-optical filter positioned in front of said objective lens;
   image intensifier means for amplifying portions of said input radiant energy transmitted by said input electro-optical filter and said objective lens, and for thereby producing an amplified electron image of the low-luminance scene;
   display screen means for generating output radiant energy constituting an amplified visible image of the low-luminance scene, in response to said amplified electron image;
   an eyepiece lens;
   an output tunable electro-optical filter disposed between said display screen means and said eyepiece lens;
   a control circuit for generating a control signal having a prescribed frequency;
   wherein said input electro-optical filter and said output electro-optical filter sequentially and synchronously transmit successive ones of a plurality of different spectral bands of said input and output radiant energy, respectively, in response to said control signal, during each successive cycle of said control signal, whereby a viewer can perceive a full-color image of the low-luminance scene when looking through said eyepiece lens.

2. The color night vision goggles as set forth in claim 1, wherein said prescribed frequency of said control signal is sufficiently high to ensure that said full-color image is flicker-free.

3. The color night vision goggles as set forth in claim 2, wherein said prescribed frequency of said control signal is in the range of between 20 Hz–180 Hz.

4. The color night vision goggles as set forth in claim 1, wherein said image intensifier means comprise an image intensifier device which includes:
   an image intensifier tube having a first face upon which said portions of said input radiant energy transmitted by said input electro-optical filter are incident, said image intensifier tube having a photocathode composed of a photosensitive material which releases electrons in response to said input radiant energy incident upon said first face; and,
   a microchannel plate provided with a multiplicity of microchannels through which pass said electrons released by said photosensitive material of said photocathode, whereby said electrons which pass through said microchannels stimulate the emission of a cascade of additional electrons, to thereby produce said amplified electron image of the low-luminance scene.

5. The color night vision goggles as set forth in claim 4, wherein said display screen means comprises a phosphor-coated second face of said image intensifier tube.

6. The color night vision goggles as set forth in claim 1, wherein said plurality of different spectral bands of said input radiant energy comprise first, second, and third spectral bands I1, I2, and I3, respectively, and said plurality of different spectral bands of said output radiant energy comprise blue, green, and red color bands, respectively.

7. The color night vision goggles as set forth in claim 6, wherein:
   said first spectral band I1 of said input radiant energy is transmitted by said input electro-optical filter during a first time interval;
   said second spectral band I2 of said input radiant energy is transmitted by said input electro-optical filter during a second time interval;
   said third spectral band I3 of said input radiant energy is transmitted by said input electro-optical filter during a third time interval;
   said blue color band of said output radiant energy is transmitted by said output electro-optical filter during said first time interval;
   said green color band of said output radiant energy is transmitted by said output electro-optical filter during said second time interval; and,
   said red color band of said output radiant energy is transmitted by said output electro-optical filter during said third time interval.

8. The color night vision goggles as set forth in claim 7, wherein said control signal comprises a ramp-shaped voltage waveform.

9. The color night vision goggles as set forth in claim 1, wherein said ramp-shaped control signal comprises a ramp-shaped voltage waveform.

10. The color night vision goggles as set forth in claim 1, wherein said at least one channel comprises first and second substantially parallel channels.

11. The color night vision goggles as set forth in claim 1, further comprising:
   a gated power supply for supplying current to said image intensifier means; and,
   an anti-laser jamming subsystem which selectively interrupts said current supplied by said gated power supply in synchronism with radiant energy from a pulsed or continuous wave jamming laser source within the field-of-view of the goggles.

12. The color night vision goggles as set forth in claim 1, further comprising:
   a gated power supply for supplying current to said image intensifier means; and,
   an anti-laser jamming subsystem which includes:
      detector means for detecting input radiant energy which lies within a particular one of said different spectral bands of said input radiant energy and which has a magnitude greater than a prescribed threshold, and for producing a detection signal in response thereto;
      means for selectively interrupting said current supplied by said gated power supply in synchronism with the transmission of said particular one of said different spectral bands of said input radiant energy by said input electro-optical filter, in response to said detection signal.

13. The color night vision goggles as set forth in claim 12, wherein said input radiant energy which lies within a particular one of said different spectral bands of said input radiant energy and which has a magnitude greater than a prescribed threshold, includes laser light generated by a continuous wave laser.

14. The color night vision goggles as set forth in claim 1, further comprising:
   a gated power supply for supplying current to said image intensifier means; and,
   a detector for detecting laser light that may enter the field-of-view of the goggles and for producing a train of electrical output pulses in response to detection of laser light, even when the detected laser light is generated by a continuous wave laser;
   a pulse-following circuit responsive to said train of electrical output pulses produced by said detector for producing a corresponding train of gating pulses; and,
   wherein said gated power supply is responsive to said gating pulses for selectively interrupting said current supplied by said gated power supply in synchronism with the detected laser pulses.

15. Color night vision goggles, comprising:
   at least one channel, each said channel including:
      an objective lens for receiving input radiant energy from a low-luminance scene within a field-of-view of the goggles;
      an input tunable electro-optical filter positioned in front of said objective lens;
      an image intensifier device for receiving and amplifying input radiant energy transmitted by said input electro-optical filter and said objective lens, and for generating output radiant energy which constitutes an amplified visible image of the low-luminance scene;
      an eyepiece lens;
      an output tunable electro-optical filter disposed between said image intensifier device and said eyepiece lens;
   a control circuit for generating a control signal having a prescribed frequency;
   wherein said input electro-optical filter and said output electro-optical filter sequentially and synchronously transmit successive ones of a plurality of different spectral bands of said input and output radiant energy, respectively, in response to said control signal, during each successive cycle of said control signal, whereby a viewer can perceive a full-color image of the low-luminance scene when looking through said eyepiece lens.

16. The color night vision goggles as set forth in claim 15, wherein said prescribed frequency of said control signal is sufficiently high to ensure that said full-color image is flicker-free.

17. The color night vision goggles as set forth in claim 15, wherein said plurality of different spectral bands of said input radiant energy comprise first, second, and third spectral bands I1, I2, and I3, respectively, and said plurality of different spectral bands of said output radiant energy comprise blue, green, and red color bands, respectively.

18. The color night vision goggles as set forth in claim 17, wherein:
   said first spectral band I1 of said input radiant energy is transmitted by said input electro-optical filter during a first time interval;
   said second spectral band I2 of said input radiant energy is transmitted by said input electro-optical filter during a second time interval;
   said third spectral band I3 of said input radiant energy is transmitted by said input electro-optical filter during a third time interval;
   said blue color band of said output radiant energy is transmitted by said output electro-optical filter during said first time interval;
   said green color band of said output radiant energy is transmitted by said output electro-optical filter during said second time interval; and,
   said red color band of said output radiant energy is transmitted by said output electro-optical filter during said third time interval.

19. The color night vision goggles as set forth in claim 15, wherein said at least one optical channel comprises first and second substantially parallel optical channels.

20. The color night vision goggles as set forth in claim 15, further comprising:
   a gated power supply for supplying current to said image intensifier device; and,
   a detector for detecting laser light that may enter the field-of-view of the goggles and for producing a train of electrical output pulses in response to detection of laser light, even when the detected laser light is generated by a continuous wave laser;
   a pulse-following circuit responsive to said train of electrical output pulses produced by said detector for producing a corresponding train of gating pulses; and,
   wherein said gated power supply is responsive to said gating pulses for selectively interrupting said current supplied by said gated power supply in synchronism with the detected laser pulses.

* * * * *